United States Patent
Czarnek et al.

(10) Patent No.: US 7,495,208 B2
(45) Date of Patent: Feb. 24, 2009

(54) PORTABLE OPTICAL WOUND SCANNER

(75) Inventors: Robert Czarnek, Johnstown, PA (US);
Brian Stroup, Pittsburgh, PA (US); Lisa Stroup, Pittsburgh, PA (US)

(73) Assignee: Czarnek and Orkin Laboratories, Inc., Highland Park, IL (US)

( * ) Notice: Subject to any disclaimer, the term of this patent is extended or adjusted under 35 U.S.C. 154(b) by 0 days.

(21) Appl. No.: 11/809,549

(22) Filed: Jun. 1, 2007

(65) Prior Publication Data

US 2007/0295888 A1    Dec. 27, 2007

Related U.S. Application Data

(60) Provisional application No. 60/809,897, filed on Jun. 1, 2006.

(51) Int. Cl.
*G01V 8/00* (2006.01)
(52) U.S. Cl. .................. 250/234; 250/235; 250/559.22; 250/559.26; 250/559.21; 600/407; 600/476; 600/477; 356/607; 356/626
(58) Field of Classification Search ............. 250/208.1, 250/234, 235, 559.22, 559.23, 559.26, 559.21; 356/626–631, 600, 601, 634, 606–608, 3.09; 600/476, 477, 424, 407; 382/128
See application file for complete search history.

(56) References Cited

U.S. PATENT DOCUMENTS

| | | | |
|---|---|---|---|
| 4,535,782 A | 8/1985 | Zoltan | |
| 5,152,757 A | 10/1992 | Eriksson | |
| 5,265,605 A | 11/1993 | Afflerbach | |
| 5,270,168 A | 12/1993 | Grinnell | |
| 5,515,156 A * | 5/1996 | Yoshida et al. | 356/5.01 |
| 5,588,428 A * | 12/1996 | Smith et al. | 600/425 |
| 5,702,356 A * | 12/1997 | Hathman | 602/41 |
| 5,749,842 A | 5/1998 | Cheong et al. | |
| 5,967,979 A * | 10/1999 | Taylor et al. | 600/407 |
| 6,381,026 B1 * | 4/2002 | Schiff et al. | 356/601 |
| 7,184,150 B2 * | 2/2007 | Quadling et al. | 356/602 |
| 7,248,724 B2 * | 7/2007 | Gutenev | 382/128 |
| 2002/0054297 A1 * | 5/2002 | Lee et al. | 356/607 |
| 2007/0276195 A1 * | 11/2007 | Xu et al. | 600/300 |

* cited by examiner

*Primary Examiner*—Stephen Yam
(74) *Attorney, Agent, or Firm*—The Webb Law Firm (57) ABSTRACT

In a wound scanning apparatus and method, a beam or sheet of light is scanned on a wound and reflections of the scanned beam or sheet of light interacting with the wound at a plurality of points thereof is detected. The detected reflections are processed into data representative of the wound. The data or a representation thereof is reproduced in a human understandable form.

16 Claims, 8 Drawing Sheets

PORTABLE OPTICAL WOUND SCANNER

CROSS REFERENCE TO RELATED APPLICATION

The present application claims priority from U.S. Provisional Patent Application No. 60/809,897, filed on Jun. 1, 2006, which is incorporated herein by reference.

BACKGROUND OF THE INVENTION

1. Field of the Invention

The present invention relates to devices for measuring the dimensions of a wound in a human or other animal, and methods for their use, and more particularly relates to an optical scanning device and method to accurately and reproducibly evaluate the dimensions of wounds.

2. Description of Related Art

When caring for patients afflicted with wounds to the flesh, such as cuts, burns, bruises, ulcerations, lacerations and the like, the extent of wound healing over time is monitored by measuring the surface area of the wound on a regular, periodic basis.

Wound monitoring for determining healing traditionally has involved recording the surface area of the untreated wound on a single transparent plastic sheet. Printed on one side of the sheet is wound sizing indicia, e.g., a grid or bullseye. The area of the wound typically is recorded by placing the printed sheet over the wound and tracing the outer boundary, or periphery, of the wound with a suitable marking device. It is important that the printed sheet, which is not sterile, not touch the area of the wound as this would introduce bacteria to the wound bed which could cause further damage to the wound. After marking, if any wound debris is on the sheet it is removed, e.g., by wiping with a suitable disinfecting or sterilizing cleanser. The size of the wound then is determined by comparing the marking with the sizing indicia. The marked sheet, which contains a sized, graphical representation of the wound, then is placed into the patient's file for future reference. This method of wound measurement has a significant degree of inaccuracy, based on the manual nature of the measurement as well as the fact that the printed sheet normally does not make direct contact with the wound.

The foregoing procedure, when repeated over a period of time, e.g., daily, thus creates a wound history for a patient. A number of these histories assembled from different patients can be used to compare the effectiveness of new wound management products and therapies with those currently available.

The use of presently available wound marking devices, however, creates potentially serious problems for the health care worker. As the device is placed over the wound, the side which faces the open wound often becomes contaminated with wound exudate, blood, necrotic tissue and the like. Contaminated devices must be cleaned and dried, and in most cases sterilized, before they can be safely handled without gloves, or stored, e.g., in a patient's file. Contaminated devices are especially dangerous when the device has been used on a patient who has a contagious disease, such as HIV, hepatitis, or on a patient whose body fluids harbor other types of infectious agents.

A number of other methods for diagnosing and treating wounds have evolved. For example, U.S. Pat. No. 5,270,168 (1993) to Grinnell measures proteases to diagnose non-healing ulcers; U.S. Pat. No. 5,152,757 (1992) to Eriksson describes a chamber and system for diagnosis and treatment of wounds; U.S. Pat. No. 5,749,842 (1998) to Cheong and Rigby discloses a packet containing a wound dressing and a method for measuring the area of a wound; U.S. Pat. No. 4,535,782 (1985) to Zoltan optically projects a visual matrix at known angles and distances into a wound allowing the volume of an ulcer to be determined; U.S. Pat. No. 5,265,605 (1993) to Afflerbach provides a wound assessment sheet and graph for tracing wound margins; and U.S. Pat. No. 5,702,356 (1997) to Hathman provides for a wound dressing that can be opened and resealed for the purpose of assessment and application of medication.

Various other methods for measuring ulcers have been employed. One such method is the utilization of a simple ruler that is placed over a wound in which its length and width are recorded. A second measurement includes the act of placing the same ruler in the vertical plane, which is inserted into a wound, resulting in a recorded depth measurement. Another method of wound assessment is to determine the volume of an ulcer by filling a tissue defect with various substances such as molding material. Once hardened, the molding material then is removed from the wound site and measured. The volume of the ulcer is equal to the volume of the hardened mold. The disadvantages of this molding method are that it is painful to a patient and disregards good sterile technique. A less painful and less accurate method to determine volume involves filling an ulcer with fluid, such as normal saline, and noting the volume of fluid used.

Still another less painful and less invasive method to measure ulcer volume utilizes stereophotogrammetic instrumentation. This method requires the exact angles of two cameras focused on a wound, followed by viewing and measuring the negatives to attain a particular ulcer volume.

Additionally, companies such as 3M and Smith & Nephew have produced transparent dressings like Tegaderm™ and Opsite™, respectively, which provide as part of their packaging material a grid to be used to measure a wound during assessment.

A major drawback to all of the above-described methods is the failure of these methods to provide a health care practitioner with accurate and reproducible measurements of a wound site.

Thus, there exists a need to provide a device and method for wound monitoring which enables the surface area dimensions of a wound to be determined accurately and reproducibly without contaminating the wound site and to minimize a health care worker's risk of exposure to contagious or infectious agents present in the wound exudate.

SUMMARY OF THE INVENTION

The present invention fulfills this need by providing a hand held optical scanning device which accurately and reproducibly measures the surface area, i.e., length, width and depth, dimensions of different types of wounds, incisions, skin tears, holes or any other skin abnormality in a human or other animal by sensing breaks on the surface of the skin.

The hand held scanning device of the present invention preferably is light-weight, narrow-bodied, easy to manipulate, non-arm and wrist fatiguing, and is supportable entirely by a user during the measurement of a wound.

Furthermore, the scanning device of the present invention does not make physical contact with the surface of the skin, ensuring that the wound site is not contaminated during the measurement process and minimizing a health care worker's risk of exposure to contagious or infectious agents present in the wound exudate.

In particular, the scanning device of the present invention includes at least one trigger button that, when depressed, emits a light beam for measuring the dimensions of a wound. The scanning device further includes at least one memory button that can display previously generated data stored on a memory chip. Also included on the scanning device is a viewing window which can display the data.

The present invention also provides a method for measuring the surface area, i.e., length, width and depth, dimensions of different types of wounds, incisions, skin tears, holes or any other skin abnormality in a human or other animal comprised of generating a light beam from the scanning device, directing the light beam towards a wound, scanning the light beam over the area of the wound, receiving a reflected light beam from the wound back into the scanning device, detecting the light intensity in the reflected light beam by means of a sensor which generates an electrical signal indicative of the detected light intensity, and processing the electrical signal into a digitized signal to generate data descriptive of the wound's length, width and depth dimensions as well as surface area and volume of the wound cavity.

In the preferred embodiment, the source of light can be a laser diode. However, an alternative source of light can be used such as a high power LED or small halogen light bulb with proper optics and means of spatial filtering.

An embodiment of the invention includes a housing and a light source disposed in said housing and operative for outputting a beam or sheet of light. Means is disposed in said housing for scanning the beam or sheet of light from said housing on a wound and a reference surface adjacent said wound. A first light sensor is disposed in said housing for detecting reflection of the scanned light that occurs in response to interaction between the scanned light with at least one of the wound and the adjacent reference surface. The first light sensor can be either a one or two-dimensional light sensor. The housing houses a means in the path of the reflected light for focusing the reflected light on the first light sensor. A controller disposed in said housing is operative for processing signals output by the first light sensor into data representative of at least the wound. A display disposed in said housing and operating under the control of the controller is operative for displaying at least one of said data and a representation thereof.

The data can include a length, width, depth area and/or volume of the wound. The representation of said data can include an image of the wound.

A mirror can be disposed in said housing for reflecting at least a portion of the scanned beam or sheet of light to the first light sensor via the focusing means. The controller can be operative for at least one of the following: for determining a direction of the scanned beam or sheet of light based on where the mirror reflected light impinge(s) on the first light sensor; or for determining a distance between the first light sensor and a surface of the wound from where the mirror reflected light impinge(s).

A screen can be disposed in said housing for reflecting a portion of the light from the mirror back thereto.

A mirror can be disposed in said housing for reflecting at least a portion of the scanned beam or sheet of light. A second light sensor can be disposed in said housing for receiving the light reflected from the mirror. The controller can be operative for processing signals output by the second light sensor into data representative of a direction of the scanned beam or sheet of light.

The housing can house a means coupled to the controller for facilitating interaction between the controller and an operator. The means for facilitating interaction can include at least one of the following: a push button; a toggle button; and a touch sensitive screen.

Means for stabilizing can be coupled to said housing for stabilizing the housing to the reference surface during scanning of the wound.

A mirror moveable under the control of a scanning motor can be provided. The beam or sheet of light output by the light source can impinge on the mirror operating under the control of the scanning motor for scanning the beam or sheet of light. When a beam of light is being scanned, the scanning means can raster scan the beam of light. When a sheet of light is being scanned, the scanning means can scan the sheet of light in one direction.

Another embodiment of the invention is a method comprising: (a) scanning a beam or sheet of light on a wound; (b) detecting reflections of the scanned beam or sheet of light interacting with the wound at a plurality of points thereof; (c) processing the detected reflections into data representative of the wound; and (d) displaying at least one of said data and a representation thereof.

The data can include a length, width, depth, area and/or volume of the wound. The representation of said data can include an image of at least part of the wound.

The method can further include reflecting at least a portion of the scanned beam or sheet of light prior to interacting with the wound, and processing the light reflected prior to interacting with the wound to determine at least one of the following: a direction of the scanned beam or sheet of light; and a distance between a surface of the wound and where the reflections of the scanned beam or sheet of light are detected.

The method can further include focusing the reflections of the scanned beam or sheet of light prior to step (b).

The wound can include an adjacent reference plane.

Lastly, an embodiment of the invention comprises: means for producing a beam or sheet of light; means for scanning the beam or sheet of light on a wound; means for detecting reflections of the scanned beam or sheet of light interacting with the wound at a plurality of points thereof; means for processing the detected reflections into data representative of the wound; and means for displaying at least one of said data and a representation thereof.

The data can include a length, width, depth, area and/or volume of the wound. The representation of said data can include an image of at least part of the wound.

A means can be provided for reflecting at least a portion of the scanned beam or sheet of light prior to interacting with the wound. Means can be provided for processing the light reflected prior to interacting with the wound to determine at least one of the following: a direction of the scanned beam or sheet of light or a distance between a surface of the wound and where the reflections of the scanned beam or sheet of light are detected.

Means can be provided for focusing the reflections of the scanned beam or sheet of light onto the means for detecting.

The wound can include an adjacent reference surface.

DETAILED DESCRIPTION OF THE INVENTION

The present invention will be described with reference to the accompanying figures where like reference numbers correspond to like elements.

Figure 1:
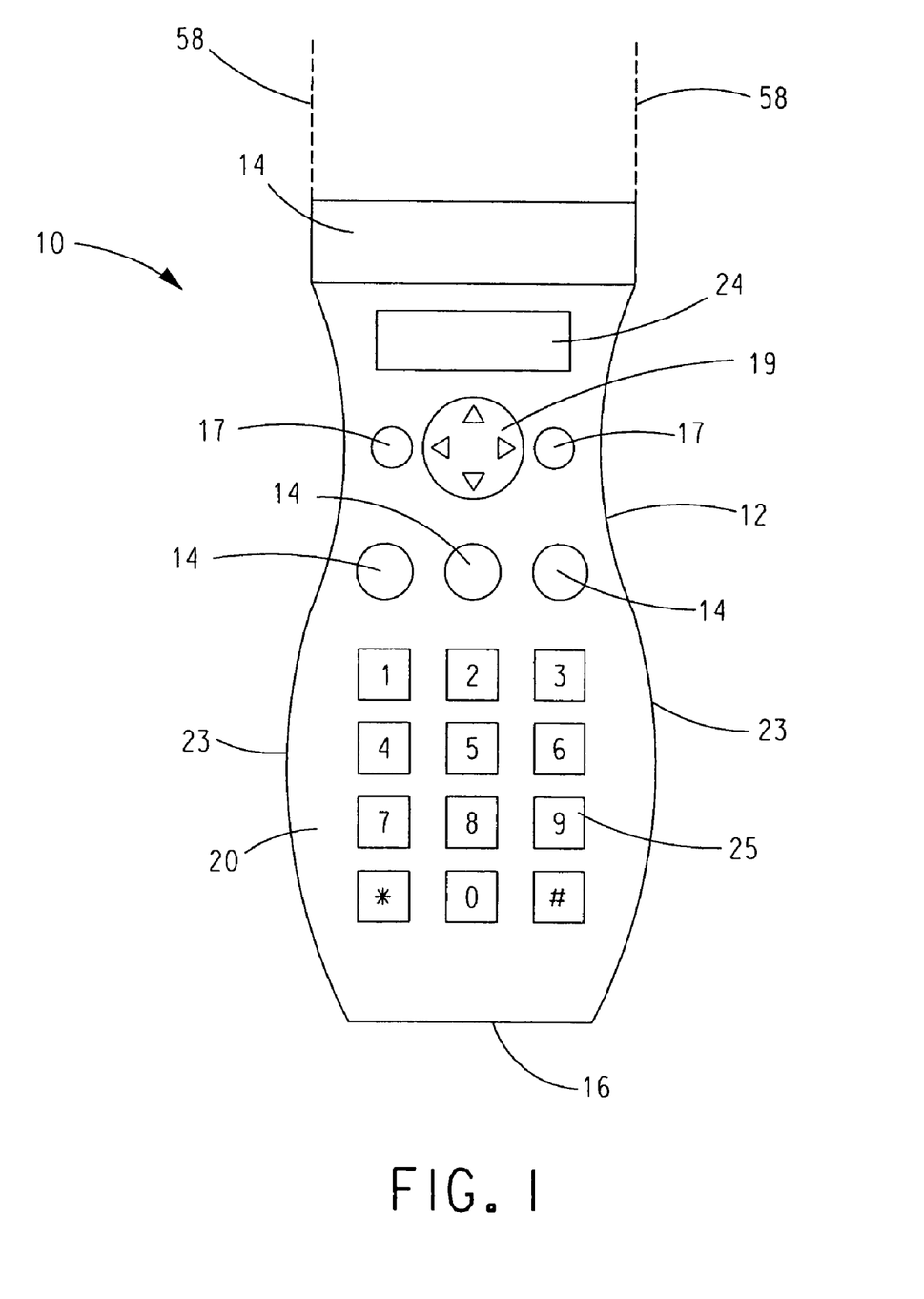
FIG. 1 is a plan view of the scanning device of the present invention.
Figure 2:
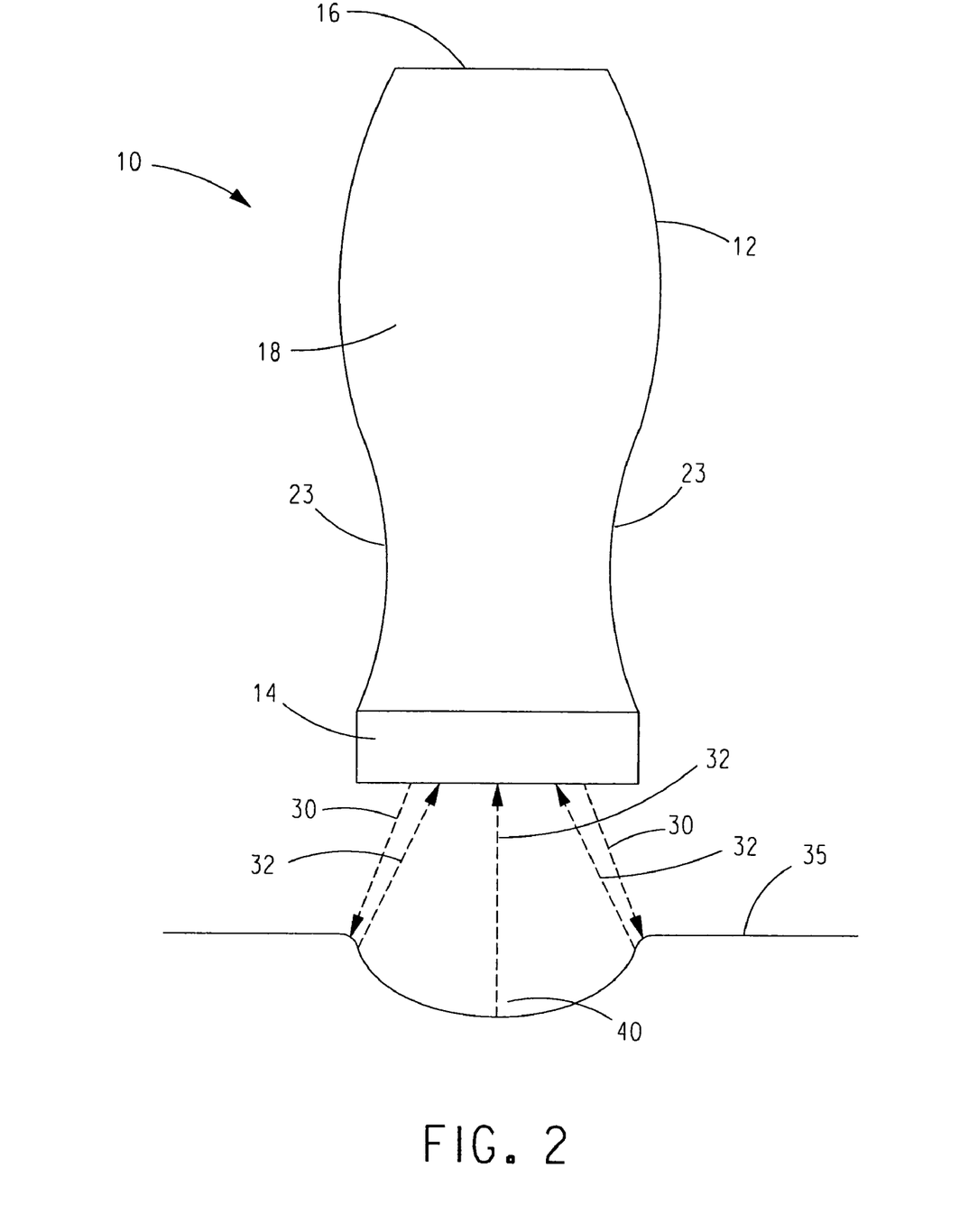
FIG. 2 is a plan view of the scanning device of the present invention showing the emittance of light onto a wound and the reflectance of light from the wound.
Figure 3:
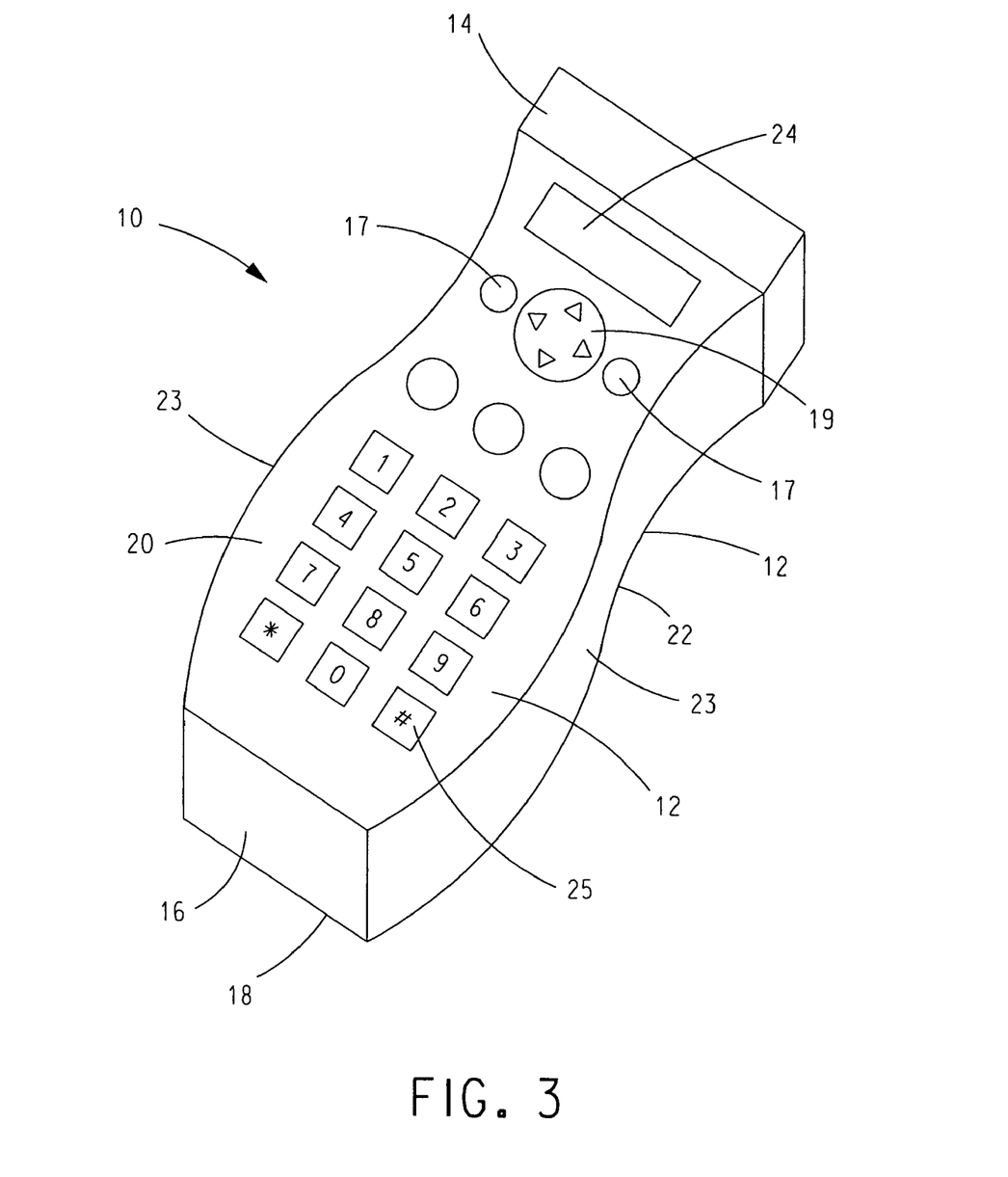
FIG. 3 is a perspective view of the scanning device of the present invention.

With reference to FIGS. 1-3, a scanning device 10 in accordance with an embodiment of the present invention includes a housing 12 having a head portion 14, a rear portion 16, a back region 18, a front region 20 and an intermediate body region 22, comprised of opposing sidewalls 23, extending between front region 20 and back region 18.

Figure 4:
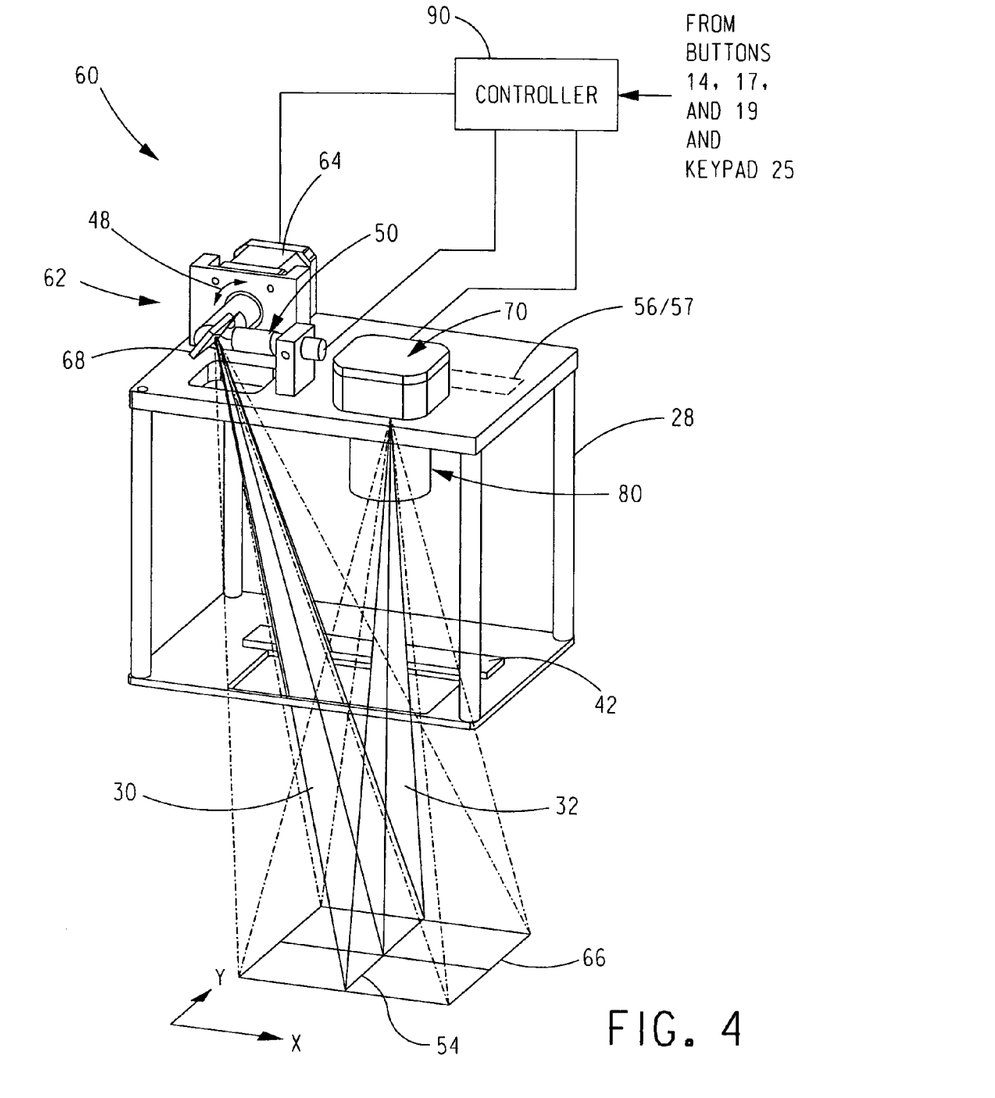
FIG. 4. is a perspective view of a light source, an optical means, a sensor means, and an imaging means supported in operative relation by a frame, all of which are included inside of the scanning device shown in FIGS. 1-3.

With reference to FIG. 4 and with continuing reference to FIGS. 1-3, scanning device 10 includes a light source 50, e.g., a miniature laser tube, a semiconductor laser diode or a high power LED, mounted within housing 12 for generating incident light 30, either in the form of a narrow beam of light or in the form of a sheet of light. Scanning device 10 also includes an optical means 60, e.g., an optical system including one or more lenses and at least one scanning mirror 68, such as, without limitation, a polygon mirror, mounted within housing 12 and operative for causing light 30 to traverse an incident light path toward a reference plane 35 located exteriorly of housing 12 in front of head portion 14, and, more specifically, toward a wound 40 located on or within reference plane 35. Incident light 30 reflecting off of wound 40 and/or reference plane 35 traverses a return light path therefrom toward head portion 14 of housing 12 as reflected light 32.

Optical means 60 can include a scanning means 62, such as, without limitation, a miniature high-speed scanning motor 64, mounted within housing 12, that can cause scanning mirror 68 to sweep or scan incident light 30 over a field of view 66 that includes wound 40 and/or reference plane 35. Alternatively, optical means can comprise an electroholographic grating of the type available from SBG Labs, Inc. of Sunnyvale, Calif.

Scanning device 10 includes a sensor means 70, e.g., a one-dimensional light sensor, a two-dimensional light sensor, or the combination of a one-dimensional light sensor and a two-dimensional light sensor, mounted within housing 12 for detecting reflected light 32 and for generating electrical signal(s) indicative of the intensity of reflected light 32.

Sensor means 70 in the form of a two-dimensional sensor can be of any suitable and/or desirable sensor technology that enables electronic signals corresponding to an optical image in the field of view of said sensor to be acquired. One non-limiting example of a sensor that can be utilized as a two-dimensional sensor in the present invention is a CCD array. Likewise, the one-dimensional sensor can be made from any suitable and/or desirable sensor technology that enables variations in light to be detected in a field of view of said sensor. One non-limiting example of such one-dimensional sensor is the "Duo-Lateral, Super Linear Position Sensing Detector" available from OSI Optoelectronics, Inc. of Hawthorne, Calif. 90250.

Scanning device 10 also includes an imaging means 80, e.g., without limitation, an objective lens, disposed in housing 12 in the path of reflected light 32 for directing and focusing reflected light 32 onto sensor means 70. The combination of sensor means 70 and lens means 80 enables bumps or breaks, e.g., wound 40, on or in reference plane 35 to be detected in a manner described hereinafter.

Scanning device 10 also includes a controller 90 disposed in housing 12 and operative for coordinating the operation of light source 50, optical means 60 and sensor means 70 to generate digital data indicative of the surface area of reference plane 35 and/or wound 40, e.g., length, width, depth area and/or volume of wound 40, and for storing or outputting said dimensions, in numerical or image form, e.g., a topographic image, on a visual display 24 housed within and viewable through housing 12, or an external display (not shown) that controller 90 communicates with via a communication port of scanning device 10, such as a USB port or an infrared port (not shown) in a manner known in the art.

Front region 20 of housing 12 can include at least one control button 15 that when activated causes the dimensions of wound 40 to be measured. In an embodiment of the present invention, one button 15 can be depressed to measure the length of wound 40, a second button 15 can be depressed to measure the width of wound 40, and a third button 15 can be depressed to measure the depth of wound 40. Alternatively, a preprogrammed sequence of measurements, such as, without limitation, length, width, depth, volume and surface area, can be performed upon activating a single button 15.

Front region 20 of housing 12 can further include one or more memory buttons 17 that can cause previously generated data stored within a memory of controller 90 to be displayed on display 24.

Front region 20 of housing 12 can include a keypad 25 for entering patient data and/or other information into controller 90. A toggle button 19, which toggles in an up, down, left or right direction, can be provided in housing 12 and coupled to controller 90 for moving from one selected data/information/function state to another.

All or part of buttons 15 and 17, toggle button 19, and/or all or part of the buttons comprising keypad 25 can be omitted and replaced by a touch sensitive screen that displays a virtual keyboard. The virtual keyboard displayed on the touch sensitive screen can include virtual buttons needed for performing a particular function. Display 24 can comprise this touch sensitive screen.

Scanning device 10 can be programmed to allow for particularized scanning of different regions of the body. For example, the name of a specific part of the body, such as, without limitation, the abdomen, coccyx, lower extremities, and upper extremities, can be entered via keypad 25, whereupon that part of the body can be scanned in which the particular contours of that body part is taken into account.

The combination of imaging means 80 and sensor means 70, in the form of a two-dimensional light sensor, can be utilized to take picture images of wound 40, which pictures can then be stored on a suitable and/or desirable memory storage device for later download into an external computer (not shown). It is contemplated that display 24 can display pictures in black and white, gray-scale, and/or in color, desirably in color.

It is contemplated that scanning device 10 weighs between about 1N to 15N (where N=Newtons), preferably about 1N to 5N, and most preferably about 1N to 3N. The size of the laser scanning device 10 can be any appropriate size which fits comfortably in the hand of a user, such as about 25 mm wide×250 mm long×125 mm deep, preferably about 250 mm wide×200 mm long×100 mm deep, and most preferably about 75 mm wide×150 mm long×70 mm deep.

Desirably, scanning device 10 includes an internal power supply, such as one or more batteries, for supplying electrical power to the various means of scanning device 10 requiring electrical power. If desired, said one or more batteries can be rechargeable and housing 12 can include an appropriate connector for connecting said rechargeable batteries to an external source of charging electrical power.

With ongoing reference to FIG. 4, in an embodiment of the present invention, sensor means 70 is a two-dimensional light sensor and imaging means 80 includes any number or combination of lens and/or mirrors, e.g., an objective lens, to capture reflected light 32 scattered from reference plane 35 and/or wound 40 in field of view 66. In this embodiment, light source 50 is a laser diode that outputs a line of light to scanning mirror 68 of optical means 60. Scanning mirror 68 is coupled to a scanning motor 64 of optical means 60 which, under the control of controller 90, causes the line of light 30 output by light source 50 to scan reference plane 35 and/or wound 40 in field of view 66 as a sheet of light 30.

The x and y axes of the two-dimensional light sensor comprising sensor means 70 can be positioned parallel to the x and y axes, respectively, of field of view 66. However, this is not to be construed as limiting the invention since it is envisioned that the axes of the two-dimensional light sensor comprising sensor means 70 can be positioned in any suitable and/or desirable alignment with respect to the axes of the field of view 66 to facilitate collecting reflected light 32 emanating from reference plane 35 and/or wound 40.

At each point in the scan of the sheet of light 30, said light 30 and reflected light 32 traveling toward imaging means 80, i.e., the light reflected by reference plane 35 and/or wound 40 in field of view 66 in response to interaction with light 30, intersect at an angle at said point on plane 35 and/or wound 40. This angle, in combination with the direction of light 30 with respect to the orientation of a frame 28 that supports light source means 50, optical means 60, sensor means 70 and imaging means 80, in operative relation enables calculation of the distance between sensor means 70 and said point using well-known triangulation methods.

The direction of light 30 with respect to frame 28 can be determined by way of a resolver and/or an encoder of scanning motor 64 which is utilized to scan sheet of light 30 by way of adjusting the position of scanning mirror 68 in a manner known in the art. Also or alternatively, a mirror 42 can be disposed between scanning mirror 68 and field of view 66 with its longitudinal axis positioned parallel to an axis, e.g., the x-axis, of field of view 66 as shown in FIG. 4. Where sensor means 70 is a two-dimensional light sensor, e.g., in the form of a two-dimensional pixilated array, a portion of light 30 in the form of a sheet of light, can be caused to strike mirror 42, whereupon said light portion is reflected directly or indirectly to one or more pixels along the edge of sensor means 70. The use of mirror 42 fixed to frame 28 in combination with light 30 and sensor means 70, in the form of the two-dimensional pixilated array, also fixed to frame 28, enables controller 90 to accurately determine the direction of light 30 and, hence, the current position of mirror 68. Based upon the direction of light 30 as detected by way of mirror 42 and edge pixels of sensor means 70, along with reflected light 32 detected by other pixels of sensor means 70, the distance between sensor means 70 and reference plane 35 and/or wound 40 can be determined by controller 90.

Figure 5:
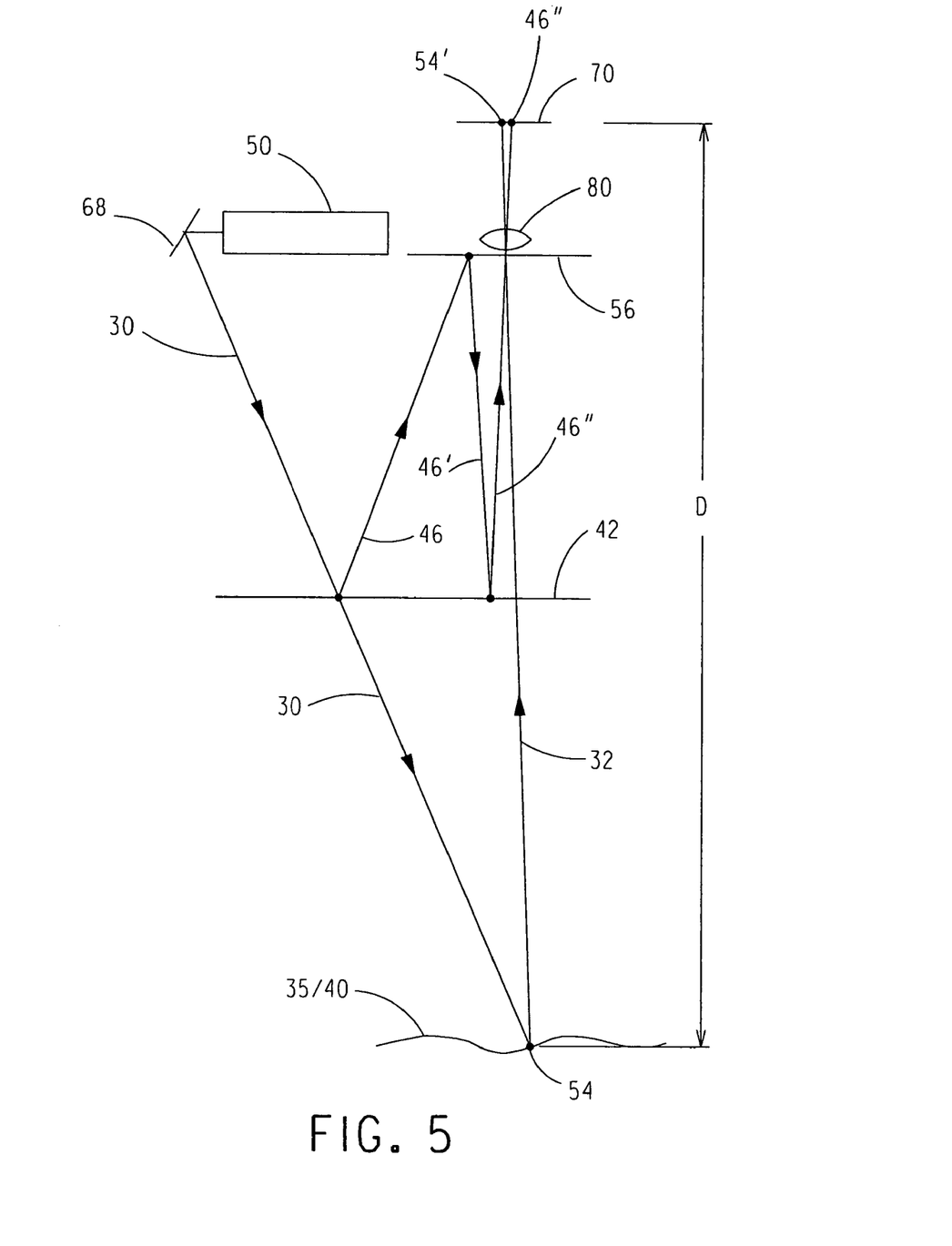
FIG. 5 is a schematic drawing showing various paths of light produced in use of the light source, optical means, sensor means and imaging means shown in FIG. 4.

For example, as shown in FIG. 5, the portion of light 30 in the form of a sheet of light striking mirror 42 is reflected thereby. This reflected light is shown in FIG. 5 by reference numeral 46. In response to interaction with a projection screen 56 disposed adjacent imaging means 80, a portion of reflected light 46 is scattered back to mirror 42. This portion of reflected light 46 is shown in FIG. 5 by reference numeral 46'. In response to scattered light 46' striking mirror 42, scattered light 46' is reflected back toward imaging means 80. The portion of scattered light 46' reflected toward imaging means 80 is shown in FIG. 5 by reference numeral 46". Light 46' and 46" are shown for the purpose of illustration and are not to be construed as limiting the invention since it is envisioned that light can be reflected back and forth between projection screen 56 and mirror 42 any number of times as necessary in order to enter imaging means 80.

Screen 56 is made from material similar to that of screens utilized to project video images on, e.g., the screen of a projection system. Because screen 56 is not a perfect reflector, light scattered thereby does not travel in a particular path. For purpose of describing the present invention, however, each path of light 46, 46' and 46" represents one ray (e.g., the central ray) of light being reflected by the respective surface.

In response to interaction with imaging means 80, reflected light 46" is directed to one or more pixels of sensor means 70 in the form of the two-dimensional pixilated array, desirably along an edge thereof. In contrast, the portion of light 30 striking reference plane 35 and/or wound 40 is reflected thereby as reflected light 32 toward imaging means 80 which focuses reflected light 30 on other pixels of sensor means 70 in the form of the two-dimensional pixilated array.

Figure 6A:
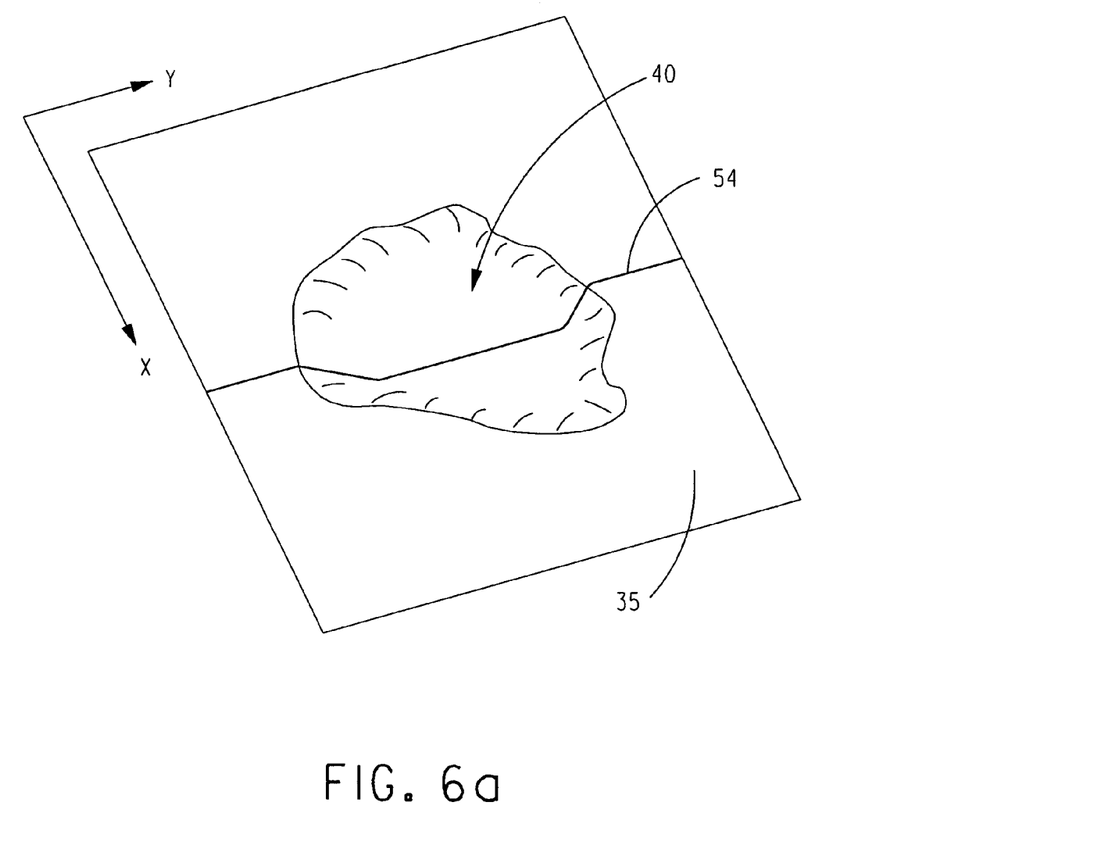
FIG. 6a is a perspective view of the scanning of a wound and surrounding reference plane with a line of light produced by the light source and optical means shown in FIG. 4.
Figure 6B:
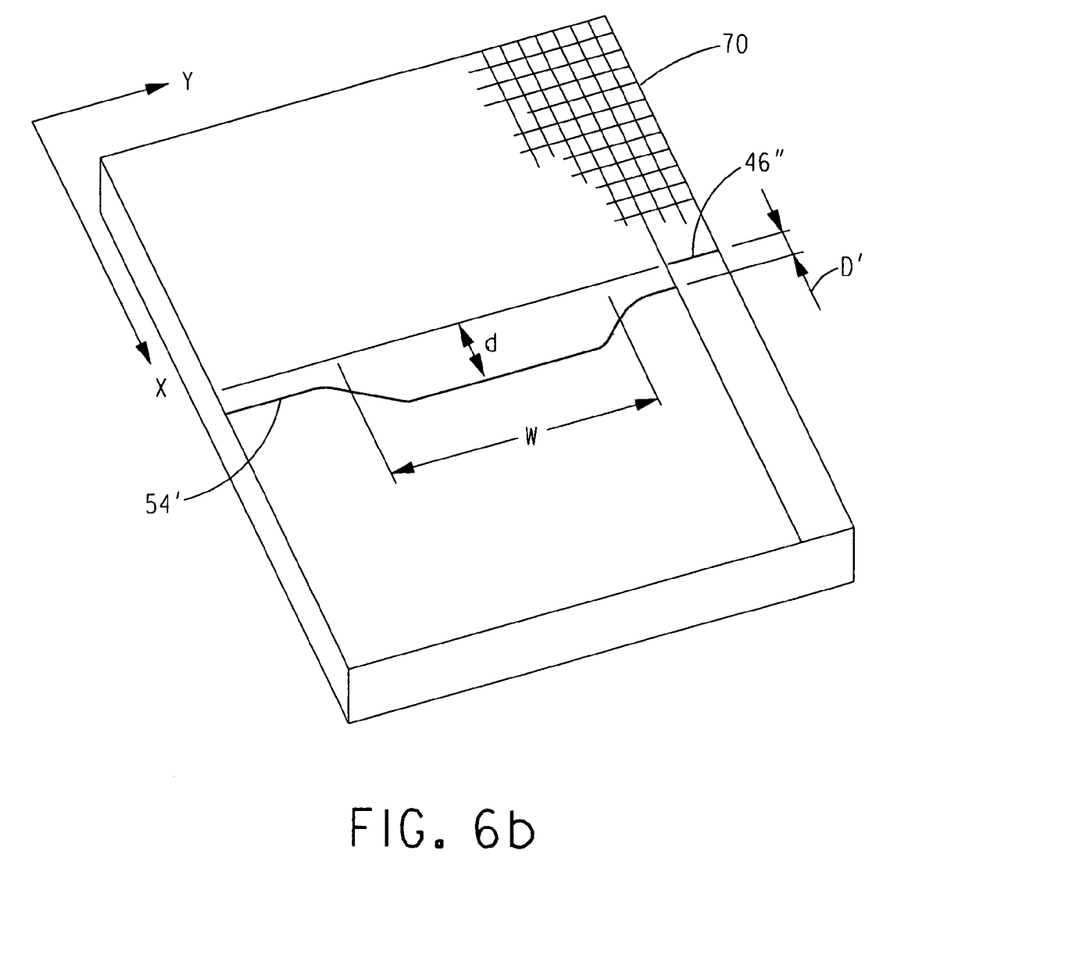
FIG. 6b is a schematic view of a two-dimensional pixilated sensor array showing the reflection of the line of light in FIG. 6a thereon, along with the reflection of a reference line of light in edge pixels of the array.

With reference to FIGS. 6a and 6b, and with continuing reference to FIGS. 4 and 5, when light 30 in the form of a sheet of light impinges on reference plane 35 and/or wound 40, a line 54 is defined thereon as shown in FIG. 6a. Because light 30 impinges on wound 40 and the adjacent reference plane 35 at an angle, line 54 will have a cup-like shape when viewed normal to reference plane 35. This is because the portion of line 54 impinging on the surface of wound 40 travels a greater distance than the portion of light 30 of line 54 impinging on reference plane 35. As shown in FIG. 6b, a portion of the light of line 54 reflected by reference plane 35 and/or wound 40 is reproduced as a line 54' on the two-dimensional pixilated array forming sensor means 70.

The depth and width of the portion of wound 40 impinged by line 54 in FIG. 6a can be determined from the corresponding depth d and width w of the corresponding line 54' striking pixels of the two-dimensional pixilated array forming sensor means 70. In order to accurately determine the depth and width of the portion of wound 40 touched by line 54, it is also necessary to know the distance D between each point of line 54 and the pixel(s) of sensor means 70 detecting said point. This distance D can be determined as a function of the distance D' (FIG. 6b) along the x-axis of sensor means 70 between where reflected light 46" strikes edge pixels of sensor means 70 and each point of line 54' strikes other pixel(s) of sensor means 70 utilizing empirical or theoretical (mathematical) techniques.

Regarding determining distance D theoretically, this distance D can be determined based upon the geometric and trigonometric relationships between the angle of light 30, and reflected light 46, the angle between light 30 and reflected light 32, along with the point on mirror 68 where light 30 originates, the point where light 30 strikes reference surface 35 and/or wound 40, the center of imaging means 80 and distance D' (FIG. 6b). It is envisioned that one of ordinary skill in the art could readily determine distance D theoretically. Accordingly, details regarding how distance D is determined from the various geometric and trigonometric relationships of light rays shown in FIG. 5 and distance D' shown in FIG. 6b will not be described herein in detail for simplicity of description.

Alternatively to having mirror 42 project reflected light 46" onto pixels adjacent the periphery of sensor means 70 in the form of a two-dimensional pixilated array, a second light sensor 57, e.g., a one-dimensional light sensor can be positioned adjacent sensor means 70 in replacement of screen 56 and can be coupled to controller 90. In an embodiment including light sensor 57, sensor means 70 in the form of a two-dimensional pixilated array can be utilized to detect only reflected light 32, while light sensor 57 can be utilized to detect reflected light 46" from mirror 42.

Where light 30 is a narrow beam of light, scanning mirror 68 can be controlled to scan light 30 in both the x and y axes of field of view 66 in what is known as a raster scan. Where it is desired that light 30 be a sheet of light, light source means 50 can be equipped with a so-called line generator (not specifically shown) which causes the light output by light source means to be in the form of a line impinging on scanning mirror 68. Hence, by simply rotating mirror 68 in the directions shown by two-headed arrow 48 in FIG. 4, line 54 of light 30 can be made to traverse field of view 66 in the x-direction as shown in FIG. 4.

Where sensor means 70 is a two-dimensional pixilated array, sensor means 70 can be operative for capturing a complete image of wound 40, and, if desired, at least a portion of the surrounding reference plane 35 in field of view 66 in response to being exposed to polychromatic light from a suitable source thereof. Thus, it is envisioned that a polychromatic image of wound 40 and at least a portion of the surrounding reference plane 35, along with data regarding the depth of wound 40 at multiple points thereof relative to reference plane 35 can be acquired in any desired order.

Imaging means 80 can be an objective lens. However, this is not to be construed as limiting the invention since imaging means 80 can include any suitable and/or desirable number or arrangement of lenses and/or mirrors deemed suitable and/or desirable by one of ordinary skill in the art to accomplish the focusing of reflected light 32 (reflected light 46") onto pixels of sensor means 70.

An obvious advantage of utilizing light 30 in the form of a sheet light that projects a line 54 versus light 30 in the form of a narrow beam of light that is raster scanned is that all of the points forming line 54 can be analyzed simultaneously by the pixels of sensor means 70 in the form of a two-dimensional pixilated array and light 30 needs to move in only one direction rather than in a raster. This not only simplifies the scanning system complexity but also increases the measurement speed.

It is envisioned that scanning device 10 can be utilized as a handheld instrument or it can be supported by any suitable and/or desirable external structure. Scanning device 10 can include one or more prongs 58 (shown in phantom in FIG. 1), that extend outward from head portion 14, that when pressed against the healthy tissue (skin) comprising reference plane 35 would help stabilize scanning device 10 during measurement. To prevent cross-contamination between patients, the tip of each prong 58 can be covered with disposable sleeves (not shown), therefore eliminating direct contact between the instrument and a patient.

Figure 7:
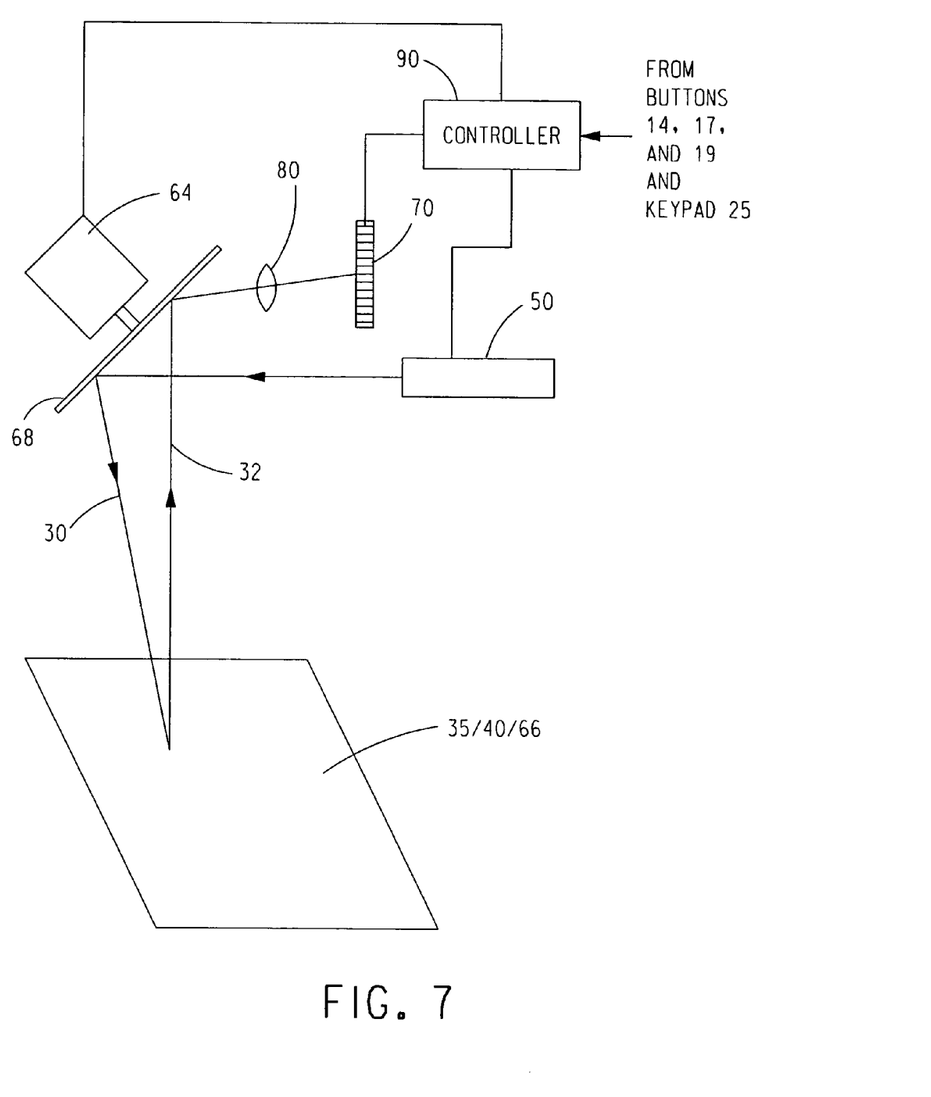
FIG. 7 is another embodiment of the present invention that includes a one-dimensional sensor in combination with the imaging means and scanning mirror of the embodiment shown in FIG. 4 arranged in a different manner to facilitate raster scanning of a surface being interrogated and the collection of data from the raster scanned surface.

With reference to FIG. 7, in an embodiment of the invention, sensor means 70 can be a one-dimensional sensor that is utilized in combination with incident light 30 in the form of a narrow beam of light. In this embodiment, light source 50 outputs a narrow beam of light which is reflected by mirror 68 toward reference plane 35 and/or wound 40 in the manner described above. In the manner described above, scanning motor 64 is controlled to cause scanning mirror 68 to raster scan incident light 30 across reference plane 35 and/or wound 40 in field of view 66. At each point in the raster scan of incident light 30, an instance of reflected light 32 is generated in response to interaction between incident light 30 and the surface of reference plane 35 and/or wound 40 where incident light 30 impinges.

Each such instance of reflected light 32 is reflected by mirror 68 imaging lens means 80 which focuses said instance of reflected light 32 onto sensor means 70 in the form of a one-dimensional light sensor. The output of sensor means 70 at each point in the raster scan of incident light 30 can be processed by controller 90 to produce data and/or images regarding reference plane 35 and/or wound 40 in field of view 66. The location and arrangement of imaging means 80 and sensor means 70 in the form of a one-dimensional light sensor in FIG. 7 can be utilized in replacement of the imaging means 80 and sensor means 70, in the form of a two-dimensional light sensor, in FIG. 4 by providing additional mounting hardware on frame 28 to support the arrangement of imaging means 80 and sensor means 70 shown in FIG. 7.

In connection with the location and arrangement of imaging means 80, and sensor means 70 and scanning mirror 68 shown in FIG. 7, it is envisioned that the combination of mirror 42 and screen 56, or the combination of mirror 42 and linear sensor 57 discussed above in connection with FIGS. 4 and 5 can be utilized therewith to enable the angle of incident light 30 to be accurately determined and, hence, the distance D to be determined between sensor means 70 in the form of a one-dimensional light sensor at each point in the raster scan of incident light 30 on reference surface 35 and/or wound 40 in field of view 66.

As can be seen, the present invention is a scanning device 10 that can comprise the combination of a sensor means 70 in the form of a two-dimensional light sensor for directly detecting reflections of incident light 30 in the form of a scanned sheet of light or a raster scanned narrow beam of light. Alternatively, scanning device 10 can include sensor means 70 in the form of a one-dimensional light sensor that receives the reflection of incident light 30 in the form of a narrow beam of light after said reflected narrow beam of light passes through imaging means 80 after being reflected by scanning mirror 68 which is also utilized to raster scan incident light 30 across the surface being interrogated.

The invention has been described with reference to the preferred embodiments. Obvious modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A wound scanning apparatus comprising:
    a housing;
    a light source disposed in said housing and operative for outputting a beam or sheet of light;
    means disposed in said housing for scanning the beam or sheet of light from said housing on a wound and a reference surface adjacent said wound;
    a first light sensor disposed in said housing for detecting reflection of the scanned light that occurs in response to interaction between the scanned light with the wound, the adjacent reference surface or both, said first light sensor being either a one- or two-dimensional light sensor;

means disposed in said housing and in the path of the reflected light for focusing the reflected light on the first light sensor;

a controller disposed in said housing and operative for processing signals output by the first light sensor into data representative of at least the wound;

a display disposed in said housing and operating under the control of the controller for displaying said data or a representation thereof; and a mirror disposed in said housing for reflecting at least a portion of the scanned beam or sheet of light to the first light sensor via the focusing means, wherein the controller is further operative for at least one of the following;

determining a direction of the scanned beam or sheet of light based on where the mirror reflected light impinge(s) on the light sensor; or determining a distance between the first light sensor and a surface of the wound based on where the mirror reflected light impinge(s) and the reflected scanned light impinge(s) on the first light sensor.

2. The apparatus of claim 1, wherein:

said data includes at least one of the following: a length, width, depth, area or volume of the wound; and said representation of said data is an image of the wound.

3. The apparatus of claim 1, further including a screen disposed in said housing for reflecting a portion of the light from the mirror back thereto.

4. The apparatus of claim 1, further including:

a second light sensor disposed in said housing for receiving the light reflected from the mirror, wherein the controller is operative for processing signals output by the second light sensor into data representative of a direction of the scanned beam or sheet of light.

5. The apparatus of claim 1, further including means supported by said housing and coupled to the controller for facilitating interaction between the controller and an operator.

6. The apparatus of claim 5, wherein the means for facilitating interaction includes at least one of the following:

a push button;

a toggle button; or a touch sensitive screen.

7. The apparatus of claim 1, further including means for stabilizing said housing to the reference surface during scanning of the wound.

8. The apparatus of claim 1, wherein:

the scanning means includes a mirror moveable under the control of a scanning motor;

the beam or sheet of light output by the light source impinges on the mirror operating under the control of the scanning motor for scanning the beam or sheet of light;

when the beam of light is being scanned, the scanning means raster scans the beam of light; and when the sheet of light is being scanned, the scanning means scans the sheet of light in one direction.

9. A wound scanning method comprising:

(a) scanning a beam or sheet of light on a wound;

(b) detecting reflections of the scanned beam or sheet of light interacting with the wound at a plurality of points thereof;

(c) processing the detected reflections into data representative of the wound;

(d) displaying said data or a representation thereof;

(e) reflecting at least a portion of the scanned beam or sheet of light prior to interacting with the wound; and (f) processing the light reflected prior to interacting with the wound to determine at least one of the following: a direction of the scanned beam or sheet of light; or a distance between a surface of the wound and where the reflections of the scanned beam or sheet of light are detected.

10. The method of claim 9, wherein:

said data includes at least one of the following: a length, width, depth, area or volume of the wound; and said representation of said data includes an image of at least part of the wound.

11. The method of claim 9, further including focusing the reflections of the scanned beam or sheet of light prior to step (b).

12. The method of claim 9, wherein the wound includes an adjacent reference plane.

13. A wound scanning apparatus comprising:

means for producing a beam or sheet of light;

means for scanning the beam or sheet of light on a wound;

means for detecting reflections of the scanned beam or sheet of light interacting with the wound at a plurality of points thereof means for processing the detected reflections into data representative of the wound;

means for displaying said data or a representation thereof;

means for reflecting at least a portion of the scanned beam or sheet of light prior to interacting with the wound; and means for processing the light reflected prior to interacting with the wound to determine at least one of the following:

a direction of the scanned beam or sheet of light; or a distance between a surface of the wound and the means for detecting.

14. The apparatus of claim 13, wherein:

said data includes at least one of the following: a length, width, depth, area or volume of the wound; and said representation of said data includes an image of at least part of the wound.

15. The apparatus of claim 13, further including means for focusing the reflections of the scanned beam or sheet of light onto the means for detecting.

16. The apparatus of claim 13, wherein the wound includes an adjacent reference surface.

* * * * *